United States Patent
Capdevila et al.

(10) Patent No.: US 7,268,353 B2
(45) Date of Patent: Sep. 11, 2007

(54) MEASURING THE MOISTURE CONTENT OF PLUTONIUM OXIDE CANISTERS

(75) Inventors: Jean-Marc Capdevila, Paris (FR); Laurent Bromet, Rueil-Malmaison (FR)

(73) Assignees: Commissariant a l'Energie Atomique, Paris (FR); Compagnie Generale des Matieres Nucleaires, Velizy Villacoublay (FR)

( * ) Notice: Subject to any disclaimer, the term of this patent is extended or adjusted under 35 U.S.C. 154(b) by 163 days.

(21) Appl. No.: 10/472,759
(22) PCT Filed: Apr. 9, 2002
(86) PCT No.: PCT/FR02/01230

§ 371 (c)(1),
(2), (4) Date: Oct. 3, 2003

(87) PCT Pub. No.: WO02/084269
PCT Pub. Date: Oct. 24, 2002

(65) Prior Publication Data
US 2004/0113091 A1    Jun. 17, 2004

(30) Foreign Application Priority Data
Apr. 11, 2001 (FR) .................................. 01 04979

(51) Int. Cl.
G01N 23/00 (2006.01)
G01T 3/00 (2006.01)
(52) U.S. Cl. .................... 250/390.05; 250/390.07; 250/391
(58) Field of Classification Search ........... 250/390.05, 250/390.01, 390.04, 390.07, 358.1, 394, 250/391; 73/73
See application file for complete search history.

(56) References Cited

U.S. PATENT DOCUMENTS 2,965,781 A * 12/1960 Gunst et al. ................. 376/154
3,602,713 A * 8/1971 Kastner et al. ............. 250/392

(Continued)

FOREIGN PATENT DOCUMENTS

JP    62116242 A * 5/1987

(Continued)

OTHER PUBLICATIONS

Holslin D et al; "A moisture probe using neutron moderation for PuO/sub 2/ canister inspection" 1998 IEEE Nuclear Science Symposium Conference Record. 1998 IEEE Nuclear Science Symposium and Medical Imaging Conference (Cat. No. 98CH36255), 1998 IEEE Nuclear Science Symposium Conference Record, Toronto, Ont., Canada, Nov. 8-14, 1998, pp. 1014-1017 vol. 2, XP002188377 1998, Piscataway, NJ, USA, IEEE, USA ISBN: 0-7803-5021-9 the whole document.

(Continued)

Primary Examiner—David Porta
Assistant Examiner—Frederick F Rosenberger
(74) Attorney, Agent, or Firm—Oblon, Spivak, McClelland, Maier & Neustadt, P.C.

(57) ABSTRACT

A process for measuring the moisture content in a quantity of $PuO_2$ powder. The process detects the content of thermal neutrons emitted by the quantity of $PuO_2$ powder and then deduces its moisture content from a value of the detected content assuming a relation determined between the proportion of thermal neutrons emitted by a quantity of $PuO_2$ powder and the known moisture content in this quantity of $PuO_2$ powder.

13 Claims, 3 Drawing Sheets

U.S. PATENT DOCUMENTS 3,955,087 A        5/1976   Ashe
5,828,069 A  *    10/1998   Umiastowski et al. .  250/390.01
6,580,079 B1 *    6/2003    Craig et al. ............  250/390.05
6,895,065 B1 *    5/2005    Lebrun et al. ..............  376/257

FOREIGN PATENT DOCUMENTS

JP           11109088 A  *  4/1999

OTHER PUBLICATIONS

Patent Abstracts of Japan vol. 005, No. 118 (P-073), Jul. 30, 1981 & JP 56 058647 A (Hitachi Ltd), May 21, 1981 abstract (English abstract only).

Patent Abstracts of Japan vol. 016, No. 019 (P-1300), Jan. 17, 1992 & JP 03 237385 A (Toshiba Corp), Oct. 23, 1991 abstract (English abstract only).

* cited by examiner

MEASURING THE MOISTURE CONTENT OF PLUTONIUM OXIDE CANISTERS

DESCRIPTION

1. Technical Domain

This invention relates to the measurement of the moisture content of plutonium oxide boxes.

2. State of Prior Art

It is essential to know the moisture content in plutonium oxide boxes before the boxes are put into storage.

The conventional method of measuring the moisture content in plutonium oxide packaged in boxes is intrusive and destructive. Therefore, it can only be used for measuring samples, since the measurement cannot be made on the entire product. Furthermore, the time necessary to obtain the results is fairly long (of the order of several days). Another disadvantage is that the measurements must be made in a specialized laboratory.

PRESENTATION OF THE INVENTION

This invention was produced to provide a nonintrusive, non-destructive method of measurements that can be used on the usage site of plutonium oxide boxes.

The principle proposed for the measurement is based on passive neutronic detection of neutrons spontaneously emitted by the plutonium oxide powder packaged in boxes. Neutrons are slowed by hydrogen atoms and particularly by hydrogen atoms in water. Therefore moisture content of plutonium oxide powder can be analyzed by evaluating the deceleration of neutrons emitted by hydrogen nuclei of water molecules contained in the plutonium oxide powder. The percentage of low energy neutrons present in the neutron emission spectrum of the powder gives the moisture content present if it is assumed that all the hydrogen atoms form part of water.

This measurement principle provides a basis for designing a measurement device to detect a moisture content in plutonium oxide powder equal to more than 0.3% by weight for a measurement duration of the order of 15 minutes. It can be checked if the 0.3% threshold is exceeded by comparing records with a reference spectrum produced for a sample with 0% moisture content (or dry spectrum).

The ambient neutron background noise can be taken into account and processed by data processing software making a spectrum subtraction from a global external neutron count made by a second measurement system.

Therefore, the purpose of the invention is a process for measuring the moisture content in a quantity of $PuO_2$ powder, characterized in that it consists of detecting the content of thermal neutrons emitted by the quantity of $PuO_2$ powder and then deducing its moisture content from this value assuming a relation determined between the proportion of thermal neutrons emitted by a quantity of $PuO_2$ powder and the known moisture content in this quantity of $PuO_2$ powder.

Advantageously, the process includes the following steps:
place the quantity of $PuO_2$ powder for which the moisture content is to be measured in a cell provided with means of shielding against thermal neutrons external to the cell, the cell also comprising neutron counting means inside the cell, measure the energy spectrum of neutrons counted by neutron counting means inside the cell for a given duration, measure ambient neutrons, counted by neutron counting means placed outside the cell, at the same time as the count is made by neutron counting means inside the cell, determine the moisture content in the quantity of $PuO_2$ powder by comparing the proportion of thermal neutrons emitted by the quantity of $PuO_2$ powder, resulting from the difference between the measurement of the energy spectrum of neutrons counted by neutron counting means inside the cell and an ambient neutron measurement function, with said determined relation between the proportion of thermal neutrons emitted by a quantity of $PuO_2$ powder and the known moisture content of this quantity of $PuO_2$ powder.

This relation between the proportion of thermal neutrons emitted by a quantity of $PuO_2$ powder and the known moisture content of this quantity of $PuO_2$ powder may be determined by evaluating the increase in the count due to the presence of a known moisture content and starting from the evaluation of the moisture content made by measurements on a quantity of reference $PuO_2$ powder with a known moisture content.

The increase in the count due to the presence of moisture may be evaluated by inserting plastic films between a quantity of reference $PuO_2$ and neutron counting means.

Advantageously, the moisture content in the quantity of $PuO_2$ powder is measured in the presence of an intense neutron source in the said cell.

Another purpose of the invention is a device for measuring the moisture content of a quantity of $PuO_2$ powder, characterized in that it comprises:
a cell provided with means of shielding against thermal neutrons external to the cell, means of receiving the quantity of $PuO_2$ powder and means of counting neutrons inside the cell, means of counting ambient neutrons placed outside the cell, means of measuring the energy spectrum of neutrons counted by neutron counting means inside the cell for a given duration, computer processing means to determine the moisture content of the quantity of $PuO_2$ powder by comparison of the proportion of thermal neutrons emitted by the quantity of $PuO_2$ powder, determined by taking the difference between the measurement of the energy spectrum of neutrons counted by neutron counting means inside the cell and an ambient neutron measurement function, with a relation determined between the proportion of thermal neutrons emitted by a quantity of $PuO_2$ powder and the known moisture content of this quantity of $PuO_2$ powder.

Preferably, the means containing the quantity of $PuO_2$ powder enable placement of a $PuO_2$ box.

Also preferably, the cell comprises means of cooling the neutron counting means inside the cell. The cooling means may include two concentric ducts composed of an inner duct and an outer duct, the inner duct comprising means of containing the $PuO_2$ box, the cell comprising means of introducing and means of evacuation of a cooling gas arranged to enable the cooling gas to circulate between the two ducts and between the inner duct and the $PuO_2$ box.

The means of counting neutrons inside the cell may consist of at least one $^3$He counter. The same applies for means of counting neutrons inside the cell.

BRIEF DESCRIPTION OF THE DRAWINGS

The invention will be better understood and other advantages and special features will become clear after reading the following description given as a nonlimitative example, accompanied by the appended drawings, wherein.

DETAILED DESCRIPTION OF EMBODIMENTS OF THE INVENTION

Figure 1:
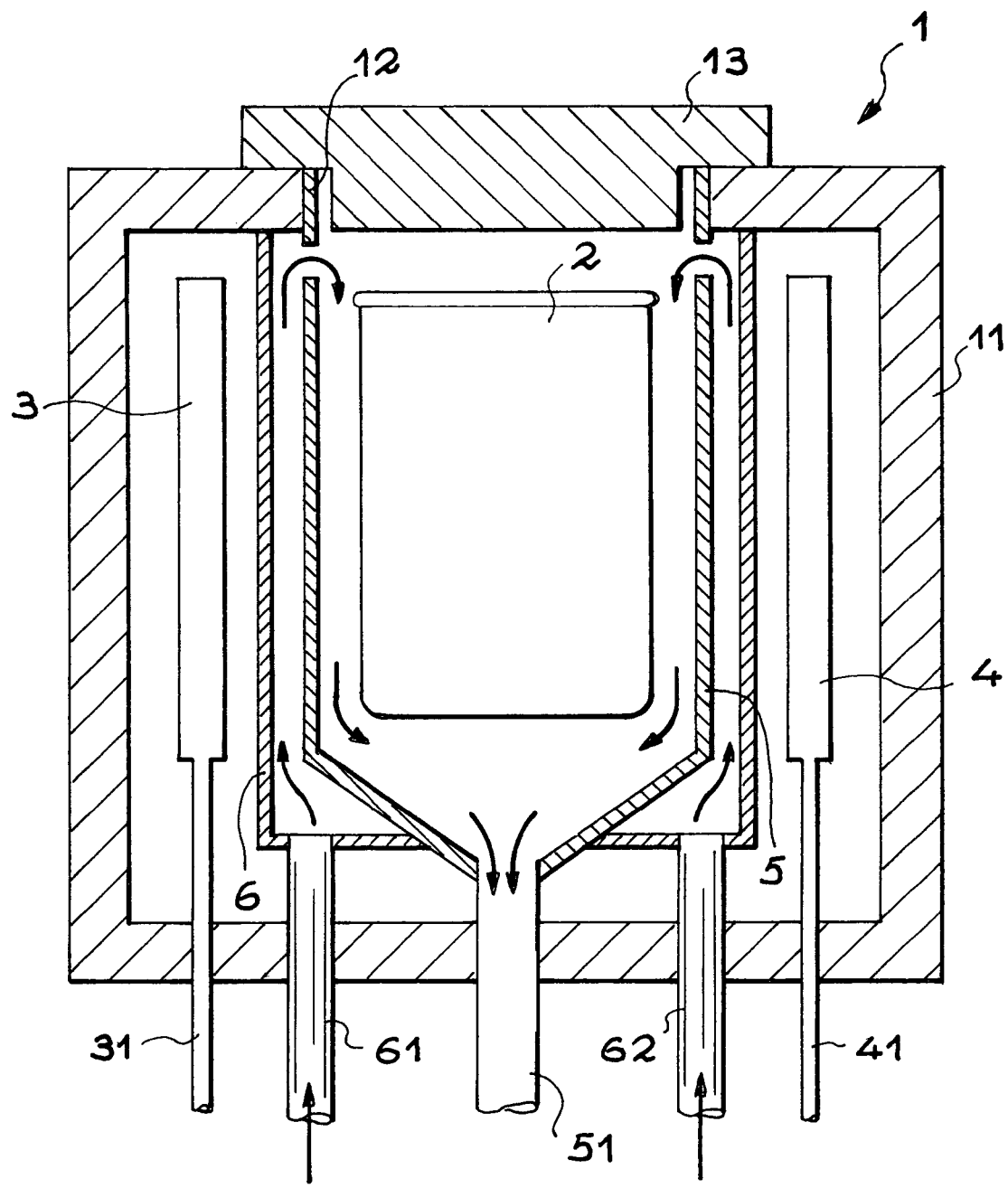
FIG. 1 is a principle diagram showing a longitudinal section of a measurement cell used to implement this invention.

FIG. 1 diagrammatically shows a longitudinal section of a measurement cell 1 used to implement this invention.

Cell 1 is sized to hold a cylindrical $PuO_2$ powder box 2, and neutron counters 3 and 4. The cell 1 may for example be parallelepiped shaped. It comprises a wall 11 in which there is an opening 12 through which the box 2 is inserted and removed. The opening 12 is closed off by a plug 13.

The cell 1 isolates the neutron counters 3 and 4 from the influence of thermal neutrons outside the cell. The objective is to minimize the neutron background noise and minimize distortion to the real spectrum output from the $PuO_2$ powder. The dimensions of cell 1 are compatible with the $PuO_2$ box and neutron counters 3 and 4. Typically, the cell may be a 35 cm×20 cm×20 cm parallelepiped.

Cell 1 may advantageously be composed of two layers of neutron absorbing materials; an inert cadmium layer to stop external thermal neutrons and a $B_4C$ blanket to eliminate epicadmic neutrons. For better efficiency, the boron carbide used must be produced using enriched boron with 96% of $^{10}B$. The recommended thicknesses are 2 mm for cadmium and 9 mm for boron carbide. The $B_4C$ used must not contain more than 5% binder or inclusions. In particular, foams (containing only 50% of $B_4C$) must not be used since they contain a large quantity of hydrogen, which has the effect of considerably increasing the background noise.

The increase in the temperature of counters 3 and 4 during the presence of a $PuO_2$ box 2 and throughout a measurement cycle can be limited by including a cooling system inside the cell 1. The following temperature conditions guarantee correct operation of the measurement system:

the temperature variation of the counters during a measurement, namely about 15 minutes, is less than 2 or 3° C.;

the temperature gradient along the counters is less than 2 or 3° C.;

the temperature variation during a measurement cycle on several consecutive boxes is less than 10° C.

FIG. 1 shows a cooling system composed of two cylindrical ducts; an inner duct 5 and an outer duct 6 that are concentric with the position of the box 2. The outer duct 6 is fixed to the upper part of the cell while the inner duct 5 is fixed to the lower part of the cell. The lower part of the outer duct 6 communicates with ducts 61 and 62 through which cooling air is brought in. Cooling air circulates between the outer duct 6 and the inner duct 5, then passes between the inner duct 5 and the box 2 to be evacuated through the cooling air evacuation duct 51.

Neutron counters 3 and 4 are advantageously $^3He$ counters located 2 cm from the $PuO_2$ box and 5 cm from the wall 11 of the cell 1. They transmit electrical signals representative of the detected neutrons to the outside, through the connecting cables 31 and 41.

The inner duct 5 is provided with elements not shown to support and center the $PuO_2$ box 2.

Figure 2:
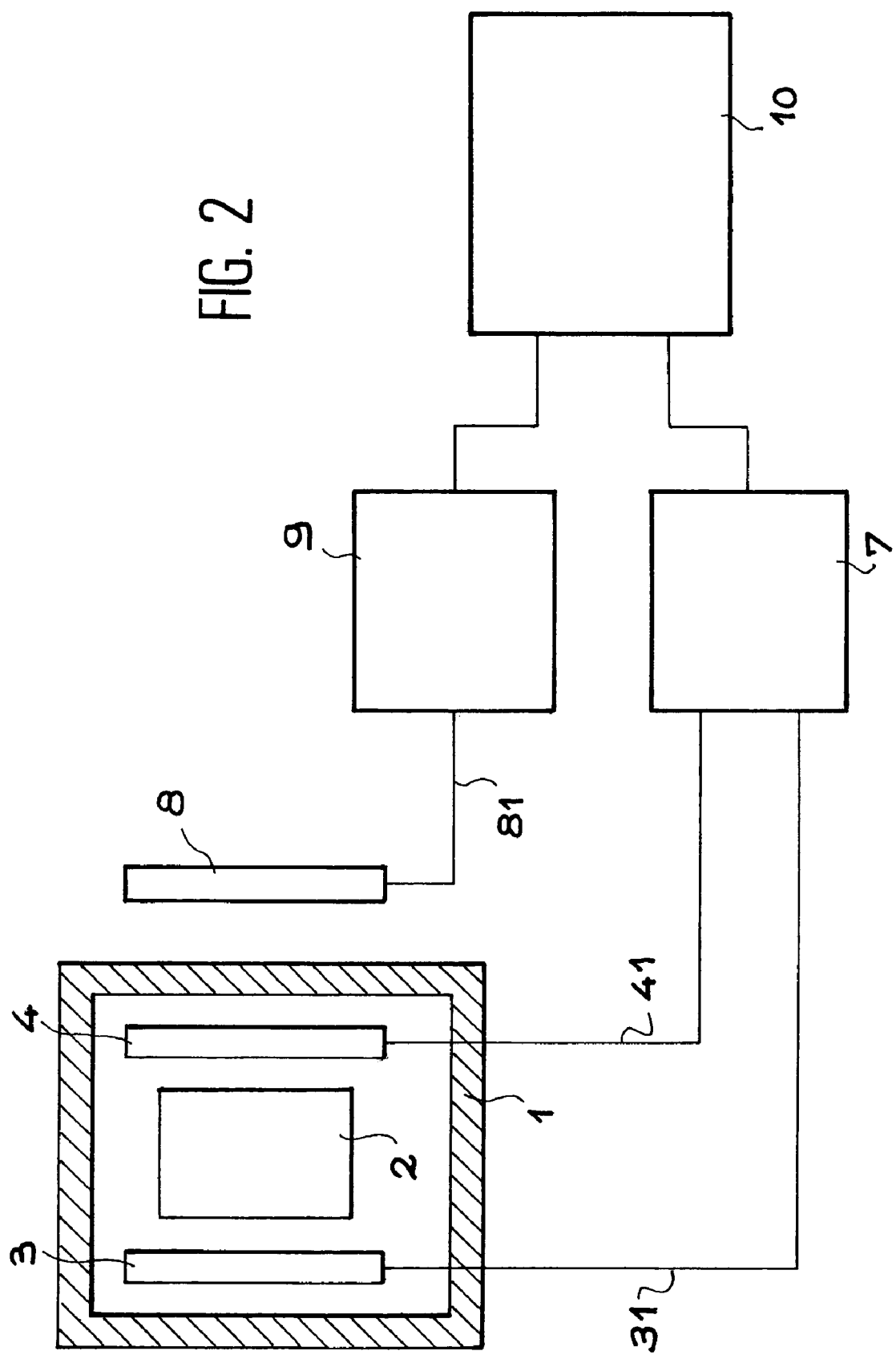
FIG. 2 is a block diagram of the device for measuring the moisture content of the quantity of $PuO_2$ powder according to this invention.

FIG. 2 is a diagrammatic view showing the measurement of the moisture content of a quantity of $PuO_2$ powder according to the invention. In this figure, the cell 1, the box 2 of $PuO_2$ powder, the neutron counters 3 and 4 and their connection cables 31 and 41 are shown briefly.

The measurement device uses a neutron acquisition system, a background noise acquisition system, and a data control and processing unit.

The neutron acquisition system comprises the two neutron counters 3 and 4 both forming part of module 7 comprising the associated electronic or processing circuits including preamplifiers, low voltage and high voltage power supplies, pulse summator, biparametric analysis card (that supplies the amplitude/rise time pair for each incoming pulse) and encoders.

The device also comprises a background noise acquisition system. If the measurement is made in a place exposed to neutrons, the background noise is an important parameter that must be controlled at all times and must be dealt with, otherwise the quality and reliability of the results will be significantly deteriorated. Normally, the best way of eliminating the background effect is to record it before starting to make the measurement (to obtain the background noise without a useful signal), to make the measurement (to obtain the background noise and the useful signal) and then to subtract one measurement from the other. However, this method cannot be used in locations in which the $PuO_2$ boxes are continuously moving. In this case, the background noises before and after the box to be measured is inserted may be completely different. Therefore the background noise must be recorded continuously, even while the box is being measured in the cell.

This can be done using a background noise acquisition system starting from a neutron counter 8 identical to those used in the cell 1 and arranged close to the cell. The counter 8 outputs a signal representative of the detected neutrons and transported by the connection cable 81 to associated electronic and processing circuits included in module 9 and including a preamplifier, a shaping amplifier, a count acquisition/scale card and the necessary high voltage and low voltage power supplies.

Modules 7 and 9 output information addressed to a data control and processing unit 10. The unit 10 includes a program developed for a PC type computer and can perform the following operations:

reinitialization or adjustment of all parameters, spectrum acquisition and measurement calibration, spectrum acquisition, processing of background noise and calculation of the moisture content, check that the device is operating correctly (cyclic between each measurement).

The measurement has to be calibrated before starting to use this measurement device according to the invention. This operation is done in two phases. The first phase consists of evaluating the increase in the count due to the presence of moisture. A second phase consists of evaluating the moisture content starting from measurements made and a reference $PuO_2$ box with a known moisture content.

Figure 3:
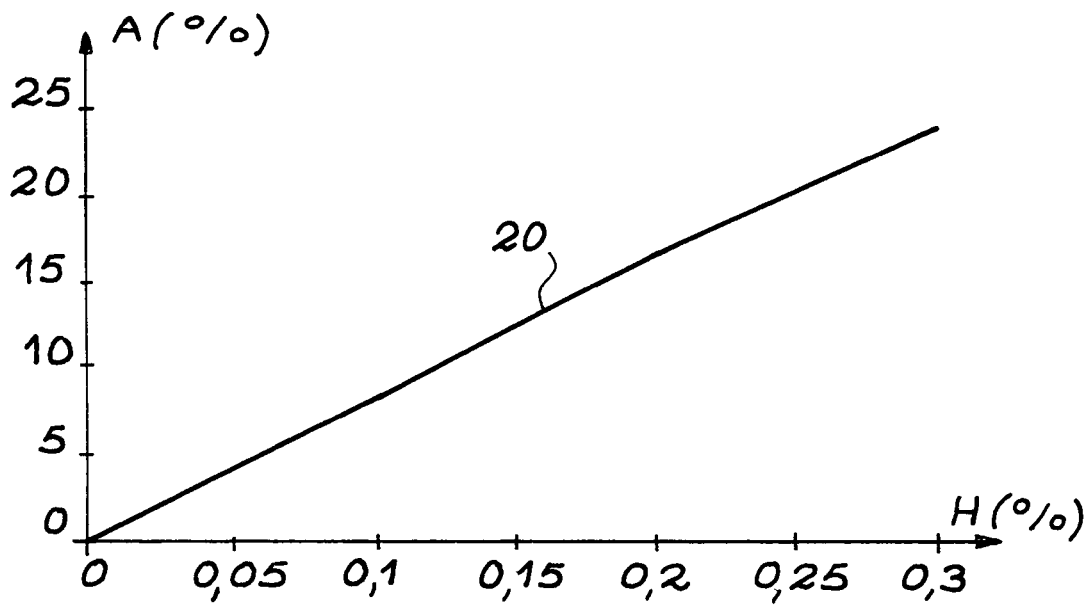
FIG. 3 is a diagram showing the variation in the increase in the neutron count as a function of the moisture content of a quantity of $PuO_2$ powder.

The first phase may be made using plastic films (PVC or polyurethane) and a $PuO_2$ box with a low moisture content (less than 0.3%), by plotting a curve like that shown in FIG. 3. The curve 20 in the diagram in FIG. 3 shows the increase in the count A in % as a function of the moisture content by mass H in %.

The second phase may be executed using two separate methods. According to a first method, two boxes with perfectly known moisture contents are available, covering the entire target measurement range (ideally from 0 to 0.3%). The next step is to measure these two boxes to obtain two reference points and the correspondence between the moisture content and the increase in the count.

According to a second method, a $PuO_2$ box is used for which the moisture content is not known accurately provided that the box is almost dry, and a set of PVC or polyurethane films with variable thickness, in order to surround the box to simulate different moisture contents. The correspondence between the increase in the moisture content and the increase in the count is then determined. All that is then necessary is to use a single reference point (for example the average moisture content on a batch) to evaluate the measurements.

Figure 4:
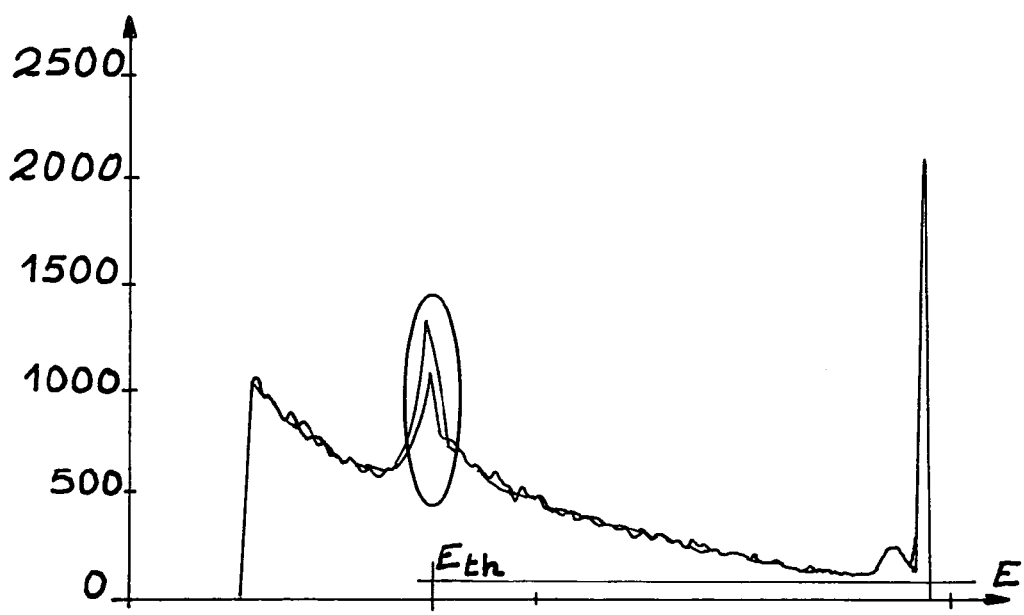
FIG. 4 is a diagram showing the energy spectra of neutrons emitted by two quantities of $PuO_2$ powder with different moisture contents.

The diagram in FIG. 4 shows the energy spectra of neutrons emitted by two quantities of $PuO_2$ powder. The ordinate axis shows the neutron count in arbitrary units. The abscissa axis represents the energy E deposited by the neutrons on the counters. The abscissa $E_{th}$ represents the most probable average energy deposited by the thermal neutrons (764 keV).

Two spectra are shown on the diagram in FIG. 4. The area on which a circle is marked comprises two peaks. The curve with the lowest peak is for $PuO_2$ powder without any trace of moisture. The curve with the highest peak is for a $PuO_2$ powder with 0.6% moisture. The moisture content is obtained by normalizing the surface of the peak for the energy channel corresponding to thermal neutrons.

The device according to the invention is capable of making a measurement lasting for 15 minutes, the time necessary to go beyond the threshold of 0.3% moisture content by mass.

Improvements can be made to obtain more precise measurements. For example, the number of counters inside the cell can be increased to increase the count rate. An intense neutron source could also be added inside the cell (up to $10^7$ n/s) to further reinforce the useful signal. This intense neutron source could be $^{252}Cf$.

The invention claimed is:

1. A process for measuring a moisture content in a quantity of $PuO_2$ powder inside a cell, comprising:
   detecting a content of thermal neutrons based on passive neutronic detection of neutrons emitted by the quantity of $PuO_2$ powder;
   determining the moisture content from a value of the detected content of thermal neutrons assuming a relation determined between a proportion of thermal neutrons emitted by the quantity of $PuO_2$ powder and a known moisture content in the quantity of $PuO_2$ powder; and
   outputting the determined moisture content.

2. The process according to claim 1, further comprising:
   placing the quantity of $PuO_2$ powder for which the moisture content is to be measured in the cell provided with shielding against thermal neutrons external to the cell, the cell also including a neutron counter inside the cell;
   measuring energy spectrum of neutrons counted by the neutron counter inside the cell for a given duration;
   measuring ambient neutrons, counted by a neutron counter placed outside the cell, at a same time as the count is made by the neutron counter inside the cell; and
   determining the moisture content in the quantity of $PuO_2$ powder by comparing a proportion of thermal neutrons emitted by the quantity of $PuO_2$ powder, resulting from a difference between the measurement of the energy spectrum of neutrons counted by the neutron counter inside the cell and an ambient neutron measurement function, with the determined relation between the proportion of thermal neutrons emitted by the quantity of $PuO_2$ powder and the known moisture content of the quantity of $PuO_2$ powder.

3. The process according to claim 2, wherein the relation between the proportion of thermal neutrons emitted by the quantity of $PuO_2$ powder and the known moisture content of the quantity of $PuO_2$ powder is determined by evaluating an increase in the count due to the presence of a known moisture content and starting from the evaluation of the moisture content made by measurements on a quantity of reference $PuO_2$ powder with a known moisture content.

4. The process according to claim 3, wherein the increase in the count due to the presence of moisture is evaluated by inserting plastic films between the quantity of reference $PuO_2$ and the neutron counter inside the cell.

5. The process according to claim 2, wherein the quantity of $PuO_2$ for which the moisture content is to be measured is arranged in a box.

6. The process for measuring moisture content according to claim 2, further comprising:
   cooling the neutron counter inside the cell.

7. The process for measuring moisture content in a quantity of $PuO_2$ powder according to claim 1, wherein said detecting is performed during a measurement cycle of less than 15 minutes and is capable of detecting a moisture content of less than 0.3% wt.

8. Device for measuring moisture content of a quantity of $PuO_2$ powder, comprising:
   a cell provided with means for shielding against thermal neutrons external to the cell, means for receiving the quantity of $PuO_2$ powder, and means for counting neutrons inside the cell by passive neutronic detection of neutrons emitted by the quantity of $PuO_2$ powder;
   means for counting ambient neutrons placed outside the cell;
   means for measuring an energy spectrum of neutrons counted by the means for counting neutrons inside the cell for a given duration; and
   computer processing means for determining the moisture content of the quantity of $PuO_2$ powder by comparison of a proportion of thermal neutrons emitted by the quantity of $PuO_2$ powder, determined by taking a difference between the measurement of the energy spectrum of neutrons counted by the means for counting neutron inside the cell and an ambient neutron measurement function, with a relation determined between the proportion of thermal neutrons emitted by the quantity of $PuO_2$ powder and the known moisture content of the quantity of $PuO_2$ powder.

9. Measurement device according to claim 8, wherein the means for receiving the quantity of $PuO_2$ powder enables placement of a $PuO_2$ box.

10. Measurement device according to claim 9, wherein the cell comprises means for cooling the means for counting neutrons inside the cell.

11. Measurement device according to claim 10, wherein the means for cooling includes two concentric ducts composed of an inner duct and an outer duct, the inner duct comprising means for containing the $PuO_2$ box, the cell comprising means for introducing and means for evacuating a cooling gas configured to enable the cooling gas to circulate between the two concentric ducts and between the inner duct and the $PuO_2$ box.

12. Measurement device according to claim 8, wherein the means for counting neutrons inside the cell includes at least one $^3$He counter.

13. Measurement device according to claim 8, wherein the means for counting neutrons outside the cell includes of at least one $^3$He counter.

* * * * *

UNITED STATES PATENT AND TRADEMARK OFFICE
CERTIFICATE OF CORRECTION

PATENT NO. : 7,268,353 B2
APPLICATION NO. : 10/472759
DATED : September 11, 2007
INVENTOR(S) : Capdevila et al.

It is certified that error appears in the above-identified patent and that said Letters Patent is hereby corrected as shown below:

On the title page, Item (73), the Assignee information is incorrect. Item (73) should read:

-- (73) Assignee: Commissariat a l'Energie Atomique, Paris, (FR)
  Compagnie Generale des Matieres Nucleaires
  Velizy Villacoublay, (FR) --

Signed and Sealed this

Twentieth Day of November, 2007

JON W. DUDAS
*Director of the United States Patent and Trademark Office*